| United States Patent [19] | [11] Patent Number: 4,551,561 |
| Stühler | [45] Date of Patent: Nov. 5, 1985 |

[54] PROCESS FOR THE PREPARATION OF POLYGLYCEROLS

[75] Inventor: Herbert Stühler, Burgkirchen, Fed. Rep. of Germany

[73] Assignee: Hoechst Aktiengesellschaft, Frankfurt, Fed. Rep. of Germany

[21] Appl. No.: 683,376

[22] Filed: Dec. 19, 1984

[30] Foreign Application Priority Data

Dec. 21, 1983 [DE] Fed. Rep. of Germany ....... 3346097

[51] Int. Cl.⁴ ............................................. C07C 41/01
[52] U.S. Cl. .................................. 568/619; 568/679; 568/680
[58] Field of Search ......................... 568/619, 679, 680

[56] References Cited

U.S. PATENT DOCUMENTS 2,110,695  3/1938  Batchelder .......................... 568/619
2,258,892  10/1941 Harris .................................. 568/679

*Primary Examiner*—Howard T. Mars
*Attorney, Agent, or Firm*—Connolly & Hutz

[57] ABSTRACT

The novel process for the preparation of polyglycerols is based on the condensation of glycerol at a temperature of 190° to 250° C. in the presence of catalysts, the water of condensation being removed. Catalysts which are used are particular compounds containing phosphorus and an alkali metal, such that 0.005 to 1% by weight, based on the weight of glycerol, of phosphorus is present and the molar ratio of alkali metal:phosphorus is 1 to 12:1.

6 Claims, No Drawings

PROCESS FOR THE PREPARATION OF POLYGLYCEROLS

The invention relates to a process for the preparation of polyglycerols with a good color quality and odour neutrality.

Polyglycerols are known as condensation products (polymerization products) which are formed from glycerol by inter-molecular removal of water and include the wide range from diglycerol (with 2 glycerol radicals or glycerol units) up to, for example, triacontaglycerol (with 30 glycerol units). The present invention essentially relates to those polyglycerols consisting of 2 to 25, preferably 2 to 15, glycerol units.

Polyglycerols are useful compounds which can be used in many ways, for example for the preparation of surface-active substances, such as esters or oxyalkylated esters. These secondary products are advantageously used as emulsifiers in the foodstuffs sector, in the formulation of cosmetics and pharmaceutical products and in the detergent sector, and as lubricants in the processing of plastics. These intended uses result in the requirement for a good color quality and odour neutrality. A process should accordingly be available, by which colorless or almost colorless polyglycerols which at the same time have as neutral as possible an odour can be prepared.

There has been no lack of attempts to achieve this aim. Starting from the earlier state of the art, according to which polyglycerols can be obtained by reaction of glycerol in the presence of alkaline or acid catalysts, the water of reaction formed during the reaction being removed, attempts have increasingly been made recently to steer this reaction to polyglycerols with the minimum possible color with the aid of particular catalysts and/or with the aid of a particular reaction procedure.

Thus, U.S. Pat. No. 3,637,774 recommends, for the preparation of polyglycerol with a good color quality, a procedure in which glycerol is reacted (condensed or polymerized) in the presence of alkaline catalysts, such as sodium hydroxide, potassium hydroxide, alkali metal alcoholates, sodium acetate, metal oxides and the like, and in the absence of water at a temperature of 100° to 300° C., the water of reaction being continuously taken off, the reaction product is cooled rapidly and taken up in water and the mixture is treated with a bleaching agent at a temperature below 100° C. and above room temperature. This process leaves much to be desired, especially since relatively highly colored polyglycerols with a strong odour (pungent odour of acrolein) are obtained if the bleaching is not carried out.

In the process described in U.S. Pat. No. 3,968,169 for the preparation of polyglycerol, (a) glycerol is heated to a temperature of 110° to 180° C. under specified temperature and pressure conditions in the presence of a catalyst system of sulfuric acid and a glycerol ester, until about 25 to 75% of the glycerol has polymerized, (b) the sulfuric acid is inactivated by addition of an essentially stoichiometric amount of a neutralizing agent and (c) the unreacted glycerol is removed by distillation. As can easily be seen, this process is relatively complicated because it requires maintenance of several specific reaction conditions. Moreover, products with a relatively poor color quality result.

The object of the present invention is accordingly to provide a process for the preparation of polyglycerols by condensation of glycerol, which leads directly to products of good color quality and with odour neutrality. The novel process should furthermore not be associated with a complicated reaction procedure, and should thus be a process which is simple in principle.

It has been found, surprisingly, that the condensation in question leads to polyglycerols with a good color quality and odour neutrality if reducing phosphorus and an alkali metal are present in a particular amount and in a particular ratio with respect to one another. Using this catalyst system, polyglycerols with an unexpectedly high color quality and odour neutrality can be obtained by a simple reaction procedure, without having to carry out a bleaching treatment.

The process according to the invention for the preparation of polyglycerols in which glycerol is reacted in the presence of catalysts at a temperature of 190° to 250° C., the water of reaction being removed, which comprises using compounds containing phosphorus and an alkali metal as the catalyst such that the phosphorus is present in an amount of 0.005 to 1% by weight, based on the weight of glycerol, and the molar ratio of alkali metal to phosphorus is 1 to 12:1, the compounds containing phosphorus and an alkali metal being selected from the group consisting of reducing phosphorus acids, alkali metal salts of reducing phosphorus acids, alkali metal hydroxides, alkali metal carbonates, alkali metal bicarbonates, alkali metal alcoholates and alkali metal oxides.

If the content of phosphorus is less than 0.005% by weight, based on the glycerol employed, the condensation reaction to give polyglycerol proceeds only very slowly. Amounts of more than 1% by weight provide no further substantial additional effect. At a molar ratio of alkali metal:phosphorus of > 12:1, relatively short reaction times are indeed possible, but the iodine color number of the resulting polyglycerol increases greatly. If this ratio is less than 1:1, the reaction of the glycerol proceeds only very slowly, even at high temperatures.

The compounds containing phosphorus and an alkali metal are preferably used in an amount such that 0.02 to 0.3% by weight (based on the weight of the glycerol employed) of phosphorus is present and the molar ratio of alkali metal:phosphorus is 2 to 5:1.

To achieve the stated amount of phosphorus and alkali metal, a procedure can be followed in which those of the compounds mentioned which contain both phosphorus and an alkali metal are employed, or in which phosphorus compounds (which contain no alkali metal) and alkali metal compounds (which contain no phosphorus) are taken. It is also possible to use compounds containing phosphorus and an alkali metal, for example $Na_2HPO_3$ or $NaH_2PO_2$, and (pure) alkali metal compounds, for example NaOH or $Na_2CO_3$. It is only important for the total stated amount of phosphorus and alkali metal to be present.

As is known, reducing phosphoric acids are those with an oxidation number (oxidation level) of +1, +3 and +4. Representatives of these are hypophosphorous acid, $H_3PO_2$ (its salts are called hypophosphites), phosphorous acid, $H_3PO_3$ (its salts are called phosphites), diphosphorous acid, $H_4P_2O_5$ (its salts are called diphosphites) and hypodiphosphoric acid, $H_4P_2O_6$ (its salts are called hypodiphosphates).

The following compounds are preferably used (individually or as mixtures) as the compounds containing phosphorus and an alkali metal: hypophosphorous acid, phosphorous acid, alkali metal salts of hypophosphorous acid, alkali metal salts of phosphorous acid, alkali metal hydroxides, alkali metal carbonates, alkali metal bicarbonates, alkali metal alcoholates, preferably methylates, ethylates and propylates, alkali metal oxides and mixtures thereof. Particularly suitable phosphorus compounds (catalyst component a) are hypophosphorous acid, phosphorous acid or mixtures thereof, and particularly suitable alkali metal compounds (catalyst component b) are alkali metal hydroxides, alkali metal carbonates, alkali metal bicarbonates, alkali metal alcoholates and alkali metal oxides, or mixtures thereof, the hydroxides, carbonates and bicarbonates being the preferred alkali metal compounds. Of the alkali metals, potassium or sodium is preferably employed.

The glycerol employed is advantageously a product of the maximum possible purity, that is to say a so-called high grade glycerol, for example the DAB8 glycerol (DAB8 = Deutsches Arzneimittelbuch (German pharmacopeia) 8th edition).

The condensation of glycerol using the catalyst system according to the invention is carried out at a temperature from 190° to 250° C., preferably 200° to 230° C. At a temperature of less than 190° C., the condensation reaction proceeds too slowly for practical use, and at above 250° C., the color quality of the condensation product decreases significantly. An inert gas atmosphere is preferably maintained during the condensation. For this, it is advantageous to stir the reaction mixture both during heating up and during the condensation and to pass an inert gas, such as nitrogen, carbon dioxide and the like, over or through the reaction mixture. The stream of inert gas is in general 0.5 to 20 liters, preferably 1 to 15 liters, of gas per hour and per kg of reaction mixture. The reaction according to the invention is as a rule carried out under atmospheric pressure or slightly decreased pressure, that is to say under a pressure of preferably 2,000 to 4,000 Pa (waterpump vacuum), any water already present and the water of reaction formed being taken off by distillation. The progress of the reaction can be monitored by measuring the amount of water of reaction and/or by determining the hydroxyl number, the refractive index, the molecular weight and/or the viscosity of the reaction product, and can be controlled to the desired degree of glycerol condensation. To end the reaction and to bring the reaction product approximately to room temperature, the product is advantageously cooled as rapidly as possible. The reaction time depends, in particular, on the reaction temperature and on the amount of phosphorus and alkali metal, as well as on the ratio of the two. It is relatively short at a high reaction temperature, with a high amount of catalyst and a high ratio of alkali metal to phosphorus.

As is known, polyglycerols, which are the reaction product of the process according to the invention, are a liquid of greater or lesser viscosity (depending on the degree of condensation) at room temperature. Apart from unreacted glycerol which may be present, the reaction product as a rule consists of a mixture of polyglycerols starting with diglycerol. Since the most useful polyglycerols comprise the homologous series with an emphasis on diglycerol to pentadecaglycerol, such a reaction product is as a rule the target. If the resulting polyglycerols are to be freed from the catalyst and the unreacted glycerol, removal of the catalyst can be achieved in a simple manner, for example by treatment of the reaction product with a basic and an acid ion-exchanger, and removal of the glycerol can be achieved in a simple manner by distillation.

The process according to the invention is simple to carry out, since it requires no special measures. The polyglycerols are obtained in an unexpectedly high color quality and odour neutrality. If an exceptional color quality is desired for the purpose of a quite specific use, this can be achieved by treating the products by methods customary for this aim, such as bleaching with active charcoal or hydrogen peroxide and/or column chromatography.

The invention will now be illustrated in detail by examples.

EXAMPLE 1

1,000 g of 98% strength by weight (that is to say 980 g of 100% strength by weight) aqueous glycerol, 0.26 g of 50% strength by weight (that is to say 0.13 g of 100% strength by weight) aqueous hypophosphorus acid and 0.32 g of 100% strength by weight sodium hydroxide (the 0.13 g of hypophosphorous acid correspond to 0.006% by weight of phosphorus, based on the 980 g of glycerol, the 0.13 g of hypophosphorous acid correspond to 0.002 mole of phosphorus and the 0.32 g of sodium hydroxide correspond to 0.008 mole of sodium; the molar ratio of sodium to phosphorus is thus 4:1) were introduced into a reaction vessel equipped with a stirrer, thermometer, gas inlet tube and reflux condenser with a water separator. The mixture was heated to 250° C. under atmospheric pressure, while stirring and passing through nitrogen (about 5 liters/hour), water already being distilled off during the heating. When the reaction temperature of 250° C. had been reached, the mixture was kept at this temperature under atmospheric pressure for 72 hours, with further stirring, passing through of the stream of nitrogen and removal of water by distillation. After this time, the reaction product had a hydroxyl number (OH number) of 1,360. It was now cooled to room temperature.

The reaction product (diglycerol according to the OH number) was a clear, almost colorless liquid. Its iodine color number was <1 (c.f. the following Table).

EXAMPLES 2 to 12

Examples 2 to 12 were carried out analogously to Example 1. The phosphorus compounds and alkali metal compounds used in each case for the reaction of the glycerol, the amounts of these compounds, the molar ratio of alkali metal to phosphorus, the reaction conditions and the hydroxyl number and iodine color number of the resulting polyglycerols are summarized in the following Table.

COMPARISON EXAMPLES 1 and 2

Comparison Examples 1 and 2 were carried out analogously to Example 1, with the exception that only sodium hydroxide (comparison Example 1) or only hypophosphorous acid (comparison Example 2) was used as the catalyst. The amount of 100% strength by weight sodium hydroxide was 1.6% by weight, and the amount of 100% strength by weight hypophosphorous acid was 0.5% by weight, based on the glycerol employed.

As the comparison examples show, the polyglycerols obtained in both cases are brown-colored, c.f. the following Table.

The iodine color number, which, as is known, serves to characterize the color of liquids, was determined in accordance with DIN (Deutsche Industrienorm (German Industrial Standard), 6162. Iodine color numbers of less than 1 (<1) to 5 result from almost colorless to lightly yellow-colored products.

The hydroxyl number, which, as is known, serves to determine the content of hydroxyl groups, was determined by the generally customary method according to DIN 53240. The relationship between the hydroxyl number and the degree of polymerization of the polyglycerol is illustrated more clearly below (c.f. the U.S. Pat. No. 3,637,774 discussed above):

| Polyglycerol | calculated hydroxyl number |
|---|---|
| Diglycerol to pentaglycerol | 1,352–1,012 |
| Hexa- to deca-glycerol | 970–888 |
| Undeca- to eicosa-glycerol | 877–825 |
| Heneicosa- to triaconta-glycerol | 821–802 |

TABLE

| | Phosphorus and alkali metal compound | | | | mole of alkali metal | Molar ratio of alkali metal to phosphorus | Reaction temperature °C. | Reaction time (hours) | Hydroxyl number | Iodine color number |
|---|---|---|---|---|---|---|---|---|---|---|
| | | mole of phosphorus | % of phosphorus | | | | | | | |
| Examples | | | | | | | | | | |
| 1 | $H_3PO_2$ | 0,002 | 0,006 | NaOH | 0,008 | 4:1 | 250 | 72 | 1360 | <1 |
| 2 | $H_3PO_2$ | 0,006 | 0,02 | KOH | 0,072 | 12:1 | 220 | 48 | 1320 | 1 |
| 3 | $H_3PO_2$ | 0,016 | 0,05 | NaOH | 0,065 | 4:1 | 230 | 27 | 1370 | 5 |
| 4 | $H_3PO_2$ | 0,030 | 0,1 | $NaHCO_3$ | 0,064 | 2,1:1 | 240 | 30 | 1360 | <1 |
| 5 | $H_3PO_2$ | 0,065 | 0,2 | NaOH | 0,065 | 1:1 | 220 | 100 | 1073 | <1 |
| 6 | $H_3PO_2$ | 0,080 | 0,25 | $CH_3ONa$ | 0,400 | 5:1 | 220 | 22 | 1167 | <1 |
| 7 | $H_3PO_2$ | 0,095 | 0,3 | NaOH | 0,950 | 10:1 | 220 | 15 | 797 | 5 |
| 8 | $H_3PO_2$ | 0,152 | 0,5 | $Na_2CO_3$ | 0,407 | 2,7:1 | 200 | 30 | 988 | 1 |
| 9 | $H_3PO_2$ | 0,318 | 1,0 | NaOH | 0,705 | 2,2:1 | 190 | 57 | 852 | 1 |
| 10 | $NaH_2PO_2$ | 0,065 | 0,2 | NaOH | 0,130 | *3:1 | 220 | 46 | 996 | 1 |
| 11 | $NaH_2PO_2$ | 0,048 | 0,15 | $Na_2CO_3$ | 0,120 | *3,5:1 | 210 | 48 | 1292 | 1 |
| 12 | $Na_2HPO_3$ | 0,080 | 0,25 | — | — | 2:1 | 230 | 55 | 923 | 1 |
| Comparison Examples | | | | | | | | | | |
| 1 | — | — | — | NaOH | 0,400 | — | 220 | 30 | 1345 | 60 |
| 2 | $H_3PO_2$ | 0,075 | 0,24 | — | — | — | 220 | 6 | 1300 | >100 |

*This value also contains the Na from the P compound.

What is claimed is:

1. A process for the preparation of a polyglycerol, in which glycerol is reacted in the presence of catalysts at a temperature from 190° to 250° C., the water of reaction being removed, which comprises using compounds containing phosphorus individually or as mixtures and compounds containing an alkali metal individually or as mixtures as the catalyst such that the phosphorus is present in an amount of 0.005 to 1% by weight, based on the weight of glycerol, and the molar ratio of alkali metal to phosphorus is 1 to 12:1, the compounds containing phosphorus and an alkali metal being selected from the group consisting of reducing phosphorus acids, alkali metal salts of reducing phosphorus acids, alkali metal hydroxides, alkali metal carbonates, alkali metal bicarbonates, alkali metal alcoholates and alkali metal oxides.

2. The process as claimed in claim 1, wherein the compounds containing phosphorus and an alkali metal are employed in an amount such that 0.02 to 0.3% by weight of phosphorus is present and the molar ratio of alkali metal:phosphorus is 2 to 5:1.

3. The process as claimed in claim 1, wherein hypophosphorous acid, phosphorous acid, alkali metal salts of hypophosphorous acid, alkali metal salts of phosphorous acid, alkali metal hydroxides, alkali metal carbonates, alkali metal bicarbonates, alkali metal alcoholates, alkali metal oxides or mixtures thereof are employed as the compounds containing phosphorus and an alkali metal.

4. The process as claimed in claim 1, wherein hypophosphorous acid, phosphorous acid or a mixture thereof is used as the phosphorus compound and an alkali metal hydroxide, alkali metal carbonate, alkali metal bicarbonate, alkali metal alcoholate, alkali metal oxide or a mixture thereof is used as the alkali metal compound.

5. The process as claimed in claim 1, wherein the reaction is carried out at a temperature from 200° to 230° C.

6. The process as claimed in claim 1, wherein hypophosphorous acid, phosphorous acid or a mixture thereof is used as the phosphorus compound and an alkali metal hydroxide, alkali metal carbonate, alkali metal bicarbonate or a mixture thereof is used as the alkali metal compound, in an amount such that 0.02 to 0.3% by weight of phosphorus is present and the molar ratio of alkali metal:phosphorus is 2 to 5:1, and the reaction is carried out at a temperature from 200° to 230° C.

* * * * *